(12) United States Patent
Richter

(10) Patent No.: US 8,508,740 B2
(45) Date of Patent: Aug. 13, 2013

(54) OPTICAL MULTI-PASS CELL

(75) Inventor: Dirk Richter, Longmont, CO (US)

(73) Assignee: University Corporation For Atmospheric Research, Boulder, CO (US)

( * ) Notice: Subject to any disclaimer, the term of this patent is extended or adjusted under 35 U.S.C. 154(b) by 687 days.

(21) Appl. No.: 12/651,549

(22) Filed: Jan. 4, 2010

(65) Prior Publication Data

US 2011/0164251 A1    Jul. 7, 2011

(51) Int. Cl.
    *G01N 21/00*    (2006.01)
(52) U.S. Cl.
    USPC ........................................... 356/440
(58) Field of Classification Search
    USPC ........................................... 356/440
    See application file for complete search history.

(56) References Cited

U.S. PATENT DOCUMENTS

| | | |
|---|---|---|
| 3,253,226 A | 5/1966 | Herriott et al. |
| 3,437,954 A | 4/1969 | Herriott et al. |
| 4,626,078 A | 12/1986 | Chernin et al. |
| 5,291,265 A | 3/1994 | Kebabian |
| 6,563,583 B2 * | 5/2003 | Ortyn et al. ............... 356/400 |
| 7,307,716 B2 | 12/2007 | Silver |
| 7,352,463 B2 * | 4/2008 | Bounaix ..................... 356/437 |

FOREIGN PATENT DOCUMENTS

EP    1 647 820 A2 *    9/2002

OTHER PUBLICATIONS

J.B. McManus, P.L. Kebabian, and M.S. Zahniser, Astigmatic mirror multipass absorption cells for long-path-length spectroscopy, manuscript, 1995 Optical Society of America, pp. 3336-3348, Applied Optics, vol. 34, No. 18, Jun. 20, 1995.

* cited by examiner

*Primary Examiner* — Tu Nguyen
(74) *Attorney, Agent, or Firm* — The Ollila Law Group LLC

(57) ABSTRACT

An optical multi-pass cell (100) including a sample cavity (109) is provided. The cell (100) also includes first and second end mirrors (103, 104) positioned within the housing (101). The mirrors (103, 104) are configured to reflect a beam of light directed at one of the first or second end mirrors (103, 104) off-axis from the optical axis (113) one or more times between the end mirrors (103, 104) through the sample cavity (109) at a first distance from the optical axis (113) to create a first beam pattern (330). The cell (100) also includes one or more relay minors (220) positioned to intercept reflect the beam of light such that at least a second beam pattern (331) is created between the end mirrors (103, 104) at a distance from the optical axis (113) different from the first distance of the first beam pattern (330).

18 Claims, 4 Drawing Sheets

OPTICAL MULTI-PASS CELL

GOVERNMENT LICENSE RIGHTS

This invention was made with Government support under ATM-0301213 and ATM-0753581 awarded by the National Science Foundation. The Government has certain rights in this invention.

TECHNICAL FIELD

The present invention is directed towards optical absorption spectroscopy. More particularly, the invention is directed towards an improved optical multi-pass cell that can be utilized in absorption spectroscopy applications.

BACKGROUND OF THE INVENTION

Absorption spectroscopy, and more particularly, laser absorption spectroscopy (LAS) is a well-known laser-based technique used for detecting and monitoring constituents in a medium, (gas, fluid, or solid). Absorption spectroscopy, in general, measures the absorption of radiation due to its interaction with a sample medium. In most cases, the absorption of one media depends upon the media constituents and their concentration. Each constituent's absorption is uniquely wavelength dependent and determined by its atomic or molecular structure and mass. Using narrow linewidth tunable laser sources, one can tune to a constituent specific absorption wavelength and determine the respective concentration present in the probed sample volume passed through by the radiation. The detection sensitivity afforded by LAS systems is typically limited by the performance of the laser source, detection techniques, constituent absorption strength and optical and electronic noise sources. A method used to enhance the signal-to-noise ratio of the LAS system is to increase the effective path length through which radiation propagates (Governed by Beer-Lambert law). For open path measurements of gaseous constituents, one can increase the physical distance between the optical source (i.e. laser) and the optical detector (typically up to several hundred meters). For in-situ sampling, this simple approach is not feasible both in terms of loading the cell with a sample for several reasons. The gas would need to be pumped through such cell and would significantly increase in the space required for storage and operation of the device.

Another approach to increase the optical path length is to provide a folded path in the form of a cell enclosing a small volume into which the media is introduced. A laser beam is introduced into such a cell composed of two opposing mirrors, in which the light is reflected back and forth multiple times through the sample cell prior to leaving the cell and reaching an optical detector. This is the basic concept provided by a so-called "Herriott Cell." The basic Herriott Cell provides two spherical end mirrors that are spaced apart from one another. A light (generally a laser) beam is introduced, typically off-axis, through a non-refracting aperture in one of the mirrors. The light is reflected back and forth between the two mirrors creating a distinct pattern. The shape of the pattern can be determined based on the physical distance between the two mirrors, the radius of curvature of the mirrors, the angle and position the light beam is injected into the cavity. As the light is reflected between the two mirrors, an effective path length that is much longer than the physical distance between the two mirrors is provided. As a result, the beams' absorption increases proportional with the distance it propagates through the sample and hence the signal-to-noise ratio of the detected light can be significantly improved.

The present invention provides an improved optical multi-pass cell with a smaller sampling volume and means to re-launch the beam into the cell after it completes a predefined propagation pattern, hence further increasing the effective length of the light path between the two end mirrors. The relay mirrors may be positioned between the two end mirrors or outside of two end mirrors. The optical source and optical detector may be positioned between the two end mirrors or outside of the two end mirrors. Further, in some embodiments, the optical multi-pass cell provides a rod or other support member between the two end mirrors. The rod can support the two end mirrors and in some embodiments house the laser source and detector. The rod can also decrease the effective sample volume between the end mirrors.

SUMMARY OF THE INVENTION

An optical multi-pass cell is provided according to an embodiment of the invention. The optical multi-pass cell comprises a housing that defines a sample cavity for receiving a sample under test. According to an embodiment of the invention, the optical multi-pass cell also includes first and second end mirrors positioned within the housing. The first and second end mirrors are separated by a distance, L, and face one another coaxially to an optical axis that extends between the first and second end mirrors. According to an embodiment of the invention, the first and second mirrors are configured to reflect a beam of light directed at one of the first or second end mirrors off-axis from the optical axis one or more times between the first and second end mirrors through the sample cavity at a first distance from the optical axis to create a first beam pattern. According to an embodiment of the invention, the optical multi-pass cell also includes one or more relay mirrors positioned to intercept the beam of light and configured to reflect the beam of light such that at least a second beam pattern is created between the first and second end mirrors. The second beam pattern is provided at a distance from the optical axis different from the first distance of the first beam pattern.

A method for forming an optical multi-pass cell is provided according to an embodiment of the invention. The optical multi-pass cell includes a housing that defines a sample cavity. The method also comprises the steps of positioning a first end mirror within the housing at a first end and positioning a second end mirror within the housing at a second end. The first and second end mirrors can be positioned such that the first and second end mirrors are separated by a distance and face one another coaxial to an optical axis that extends between the first and second end mirrors. According to an embodiment of the invention, the first and second end mirrors are configured to reflect a beam of light directed at one of the first or second end mirrors off-axis from the optical axis one or more times between the first and second end mirrors through the sample cavity at a first distance from the optical axis to create a first beam pattern. According to an embodiment of the invention, the method also comprises the step of positioning one or more relay mirrors to intercept the beam of light and reflect the beam of light such that at least a second beam pattern is created between the first and second end mirrors at a distance from the optical axis different from the first distance of the first beam pattern.

DETAILED DESCRIPTION OF THE INVENTION

FIGS. 1-4 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
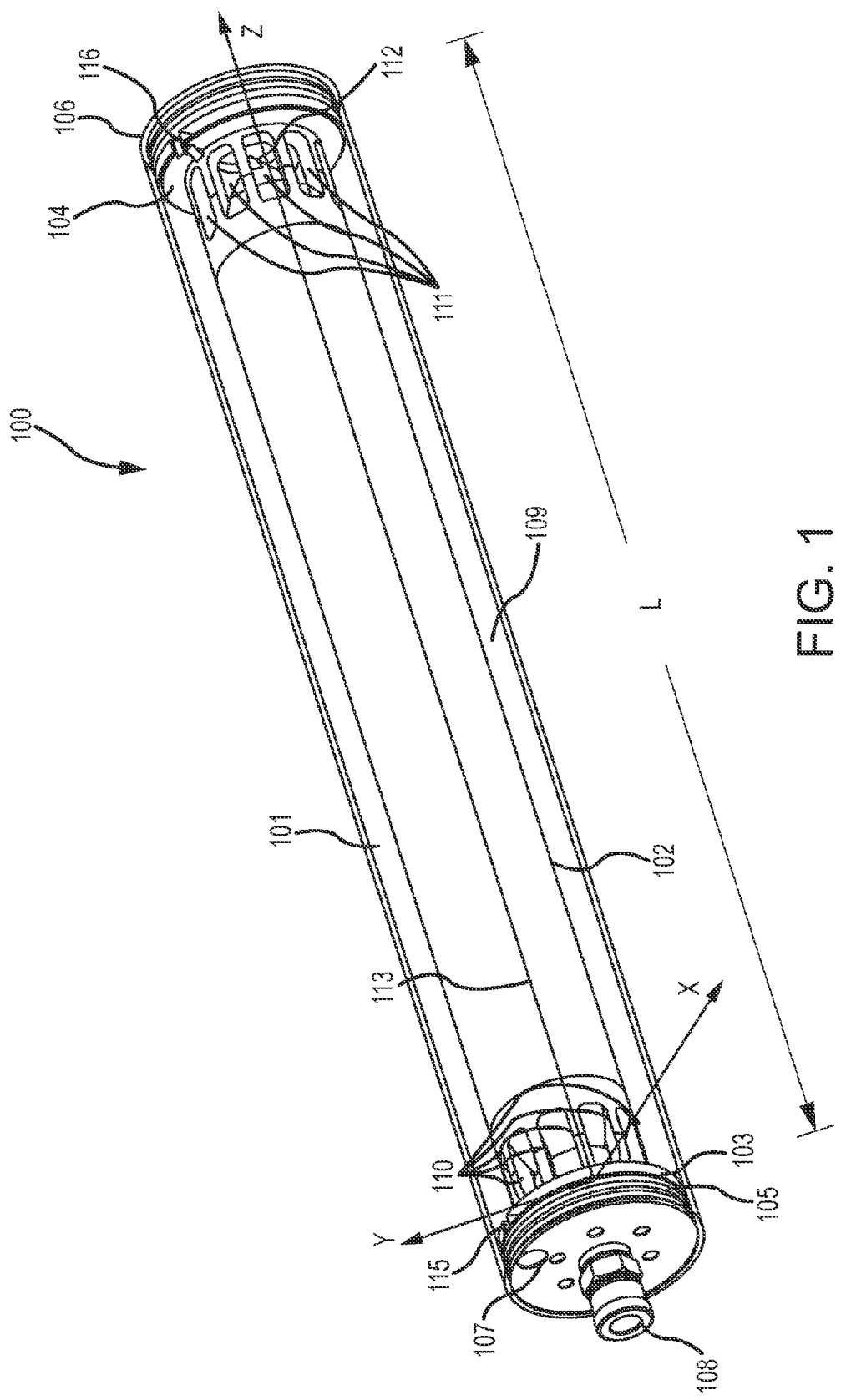
FIG. 1 shows an optical multi-pass cell according to an embodiment of the invention.

FIG. 1 shows an optical multi-pass cell 100 according to an embodiment of the invention. The optical multi-pass cell 100 shown in FIG. 1 includes a housing 101, a first end mirror 103, a second end mirror 104, and first and second end caps 105, 106. According to an embodiment of the invention, the first end cap 105 includes an optical aperture 107 and a sample aperture 108. It should be appreciated that either the optical aperture 107, the sample aperture 108 or both could be formed in the housing 101 rather than the end cap 105. According to an embodiment of the invention, the first and second end caps 105, 106 are coupled to the housing 101. According to an embodiment of the invention, a sample cavity 109 is defined by the housing 101. According to an embodiment of the invention, the first and second end mirrors 103, 104 are coupled to the first and second end caps 105, 106. According to an embodiment of the invention, the optical multi-pass cell 100 also includes a center rod 102. The center rod 102 can be coupled to the first and second end mirrors 103, 104. According to an embodiment of the invention, the center rod 102 can be positioned within the housing 101. In embodiments including the center rod 102, the center rod 102 can therefore reduce the effective volume available for the sample under test that is introduced through a sample aperture 108 formed in the first end cap 105 by the volume occupied by the center rod 102. It should be appreciated that while the center rod 102 is shown as comprising a cylindrical shape, the center rod 102 may comprise any desired shape. It should be appreciated that while the center rod 102 may be advantageous in some embodiments, other embodiments may omit the center rod 102. In embodiments omitting the center rod 102, the first and second end mirrors 103, 104 may be held in position by being coupled to the housing 101 and/or the first and second end caps 105, 106. Therefore, while the center rod 102 is shown in the drawings, some embodiments may be provided without the center rod 102 while remaining within the scope of the invention.

According to an embodiment of the invention, the center rod 102 extends along an optical axis of symmetry 113 illustrated along the z-axis using the coordinate system as shown in FIG. 1. The x and y-axis are orthogonal to each other and to the z-axis as is generally known in Cartesian coordinate systems. According to the coordinate system used, the z-axis passes through the center of the first and second end mirrors 103, 104 with the reflecting surface of the first end mirror 103 intersecting the at x=y=z=0 and the reflecting surface of the second end mirror 104 intersecting the z-axis at x=y=0, z=L, where L is the distance between the first and second end mirrors 103, 104. It should be appreciated that any coordinate system may be used and the present invention is certainly not limited to the specific coordinate system shown, but rather is provided as an example to aid in the understanding of the invention.

According to an embodiment of the invention, the first and second end mirrors 103, 104 are symmetrically positioned about the optical axis 113. According to an embodiment of the invention, the center rod 102 can be coupled to the first and second end mirrors 103, 104. The center rod 102 can therefore be used to align the first and second end mirrors 103, 104. In some embodiments, the center rod 102 may be used to maintain the position of the first and second end mirrors 103, 104.

According to an embodiment of the invention, the first and second end mirrors 103, 104 comprise spherically shaped mirrors. In embodiments where the end mirrors 103, 104 comprise spherical mirrors, meaning the radius of curvature in the x-direction ($r_x$) is substantially equal to the radius of curvature in the y-direction ($r_y$) resulting in a radius of curvature $r_{103}$ for the first end mirror 103 and a second radius of curvature $r_{104}$ for the second end mirror 104. According to an embodiment of the invention, the radius of curvature $r_{103}$ of the first end mirror 103 is substantially equal to the radius of curvature $r_{104}$ of the second end mirror 104. According to an embodiment of the invention, the first and second end mirrors 103, 104 can be spaced in an arrangement in which the beam wavefront radius nearly matches the radius of curvature of the end mirrors 103, 104. However, other arrangements are possible and the present invention should not be limited to this arrangement.

While the above discussion describes the first and second end mirrors 103, 104 as comprising spherical mirrors, it should be appreciated that the first and second end mirrors 103, 104 may comprise astigmatic mirrors, wherein the radii of curvature in the x and y-directions are not equal. However, such mirrors are often much more expensive to manufacture. Further, the astigmatism of the mirror typically creates a non-circular beam pattern because of the two different radii of curvature. As a result, if astigmatic mirrors are used, not only is a more precise alignment of the mirrors required, but the shape and/or size of the center rod 102 may need to be adjusted in order to prevent the center rod 102 from interfering with the light. Therefore, in many embodiments, spherical mirrors may be preferred over astigmatic mirrors. According to an embodiment of the invention, the first and second end mirrors 103, 104 can comprise glass substrate mirrors, which can be easily polished to a desired surface roughness and coated with either a highly reflective dielectric coating or metal coating (such as but not limited to Gold) or a combination of each.

According to an embodiment of the invention, a sample to be tested can be introduced through the sample aperture 108. The sample may comprise a gas, liquid, or solid. According to an embodiment of the invention, the sample can flow through the sample aperture 108 formed in the end cap 105, through a sample aperture 212 (See FIG. 2) in the first end mirror 103, to one or more openings 110 formed in the center rod 102 proximate the first end mirror 103. According to an embodiment of the invention, the plurality of openings 110 can disperse the sample substantially evenly throughout the cavity 109. According to an embodiment of the invention, the optical multi-pass cell 100 may omit the plurality of openings 110 and provide a single opening formed in either the center rod 102 or the first end mirror 103 outside of the center rod 102. The sample can flow through the cavity 109 towards one or more openings 111 formed in the center rod 102 proximate the second end mirror 104. The one or more openings 111 can be in fluid communication with an aperture 112 formed in the second end mirror 104 that communicates with an aperture 208 (See FIG. 2) formed in the second end cap 106 similar to the aperture 108 formed in the first end cap 105.

Figure 2:
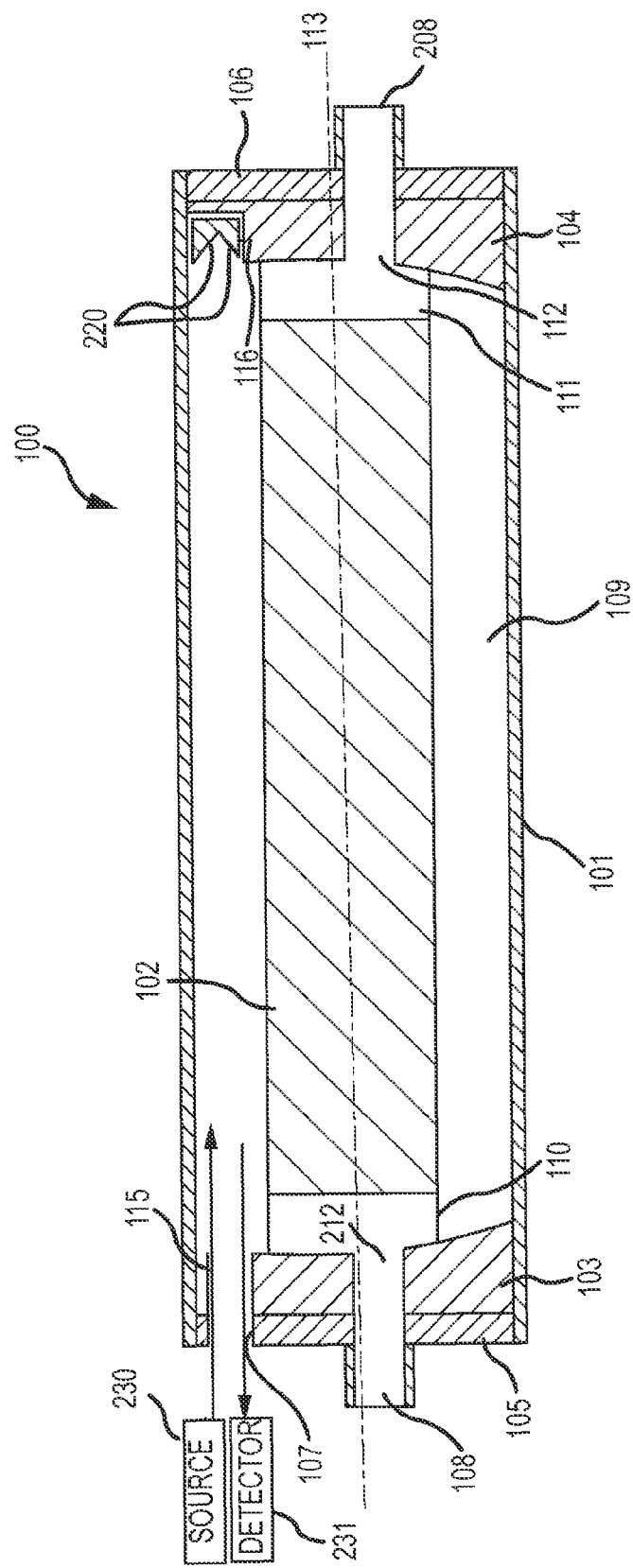
FIG. 2 shows a cross-sectional view of the optical multi-pass cell according to an embodiment of the invention.

FIG. 2 shows a partial cross-sectional view of the optical multi-pass cell 100 according to an embodiment of the invention. In the embodiment shown, the sample aperture 108 formed in the first end cap 105 extends through the first end cap 105 to an aperture 212 formed in the first end mirror 103. When a sample is introduced through the apertures 108, 212, the sample can enter the sample cavity 109 through one or more of the openings 110 formed in the center rod 102. The sample can flow through the sample cavity 109 towards the one or more openings 111 formed in the center rod 102 proximate the second end mirror 104 to exit through the aperture 112 formed in the second end mirror 104 and the second end cap 106. According to an embodiment of the invention, the sample aperture 208 formed in the second end cap 106 may be closed off during measurement in order to pressurize the sample cavity 109. While the sample cavity 109 may be pressurized to any desired pressure, according to one embodiment of the invention, the sample cavity 109 is typically pressurized to between 50 and 100 torr.

As can be seen in the embodiment shown in FIG. 2, the optical multi-pass cell 100 includes an optical source 230 and an optical detector 231. The optical source 230 may comprise any well-known device that can generate and output a beam of light. In a preferred embodiment, the beam of light comprises a coherent beam. By coherent, it is meant that the electromagnetic waves of the beam of light maintain a substantially fixed phase relationship with each other over a given period. Examples of suitable optical sources are fiber lasers, diode lasers, quantum cascade lasers, etc. Those skilled in the art will readily recognize that the particular optical source chosen will depend on a number of factors including, but not limited to the desired line width, frequency, wavelength, etc. The particular optical source 230 chosen should in no way limit the scope of the present invention. Similarly, the optical detector 231 may comprise a well-known detector that can receive and process an optical signal, such as the ability to detect photons. Examples of suitable detectors are metal-semiconductor-metal photo detectors, mercury cadmium telluride detectors, etc. Optical detectors are generally known in the art and widely used in absorption spectroscopy. Therefore, the particular optical detector 231 utilized should in no way limit the scope of the present invention. The optical source 230 and/or the optical detector 231 may be in communication with a computer or other processing system (not shown) that can be configured to process the optical signals sent and received by the optical source 230 and optical detector 231, respectively.

According to an embodiment of the invention, the optical source 230 can introduce light into the cavity 109 through the optical aperture 107 formed in the end cap 105 and the aperture 115 formed in the first end mirror 103. It should be appreciated that the optical aperture 107 formed in the end cap 105 may comprise a window or similar configuration that is optically transparent, but retains the sample under test within the sample cavity 109. Therefore, the sample cavity 109 can remain substantially sealed even in embodiments where the optical aperture 107 is provided. Similarly, while the aperture 115 formed in the first end mirror 103 is shown as a gap in the end mirror, the aperture 115 may similarly comprise an optically transparent solid structure. According to an embodiment of the invention, the light enters the sample cavity 109 off-axis from the optical axis of symmetry 113. The light travels towards the second end mirror 104. Upon reaching the second end mirror 104, the light is reflected back towards the first end mirror 103. The light travels in this manner around the first and second end mirrors 103, 104 creating a distinct beam pattern. It should be appreciated that the distance between the beam spots on a specific end mirror will depend upon the radius of curvature of the end mirrors 103, 104 as well as the distance L between the first and second end mirrors 103, 104 and the angle at which the light is introduced into the cell 100. The light will travel around the first and second end mirrors 103, 104 creating the first beam pattern at a specific distance from the optical axis 113 until the light reaches the aperture 116 formed in the second end mirror 104. According to an embodiment of the invention, the aperture 116 can be located such that the light reaches the aperture 116 prior to beam spots overlapping one another.

According to an embodiment of the invention, once the light reaches the aperture 116, the light is reflected by one or more relay mirrors 220 rather than by the second end mirror 104. While the relay mirror 220 is shown positioned within the end cap 106, it should be appreciated that in some embodiment, an optical aperture (not shown) may be provided in the second end cap 106 that aligns with the second end mirror 104 in order to allow the relay mirror 220 to be positioned outside of the end cap 106. According to an embodiment of the invention, one relay mirror 220 is shown. However, it should be appreciated that more than one pair of relay mirrors 220 may be provided. Further, more than one aperture 116 may be provided in the first or second end mirror 103, 104 in order to accommodate one or more additional relay mirrors at different locations around the first and second end mirrors 103, 104 so long as the relay mirror is positioned to intercept the beam of light prior to the light being received by the optical detector 231. Therefore, the present invention should not be limited to the position or the number of relay mirrors 220 shown in the FIG. 2.

According to an embodiment of the invention, the light is reflected off from the relay mirror 220 at an angle that is different from the angle the light is reflected off from the first and second end mirrors 103, 104. As a result, the light travels towards the first end mirror 103 and is reflected at a distance to the optical axis 113 that is different from the first distance to the optical axis 113 provided by the first beam pattern, thereby creating a second beam pattern. The light is then reflected between the first and second end mirrors 103, 104 to form the second beam pattern that is at a different distance from the optical axis 113 than previously provided. The second beam pattern may be closer or farther from the optical axis 113. The propagation between the first and second end mirrors 103, 104 repeats and travels around the mirrors 103, 104 until the light reaches the optical aperture 115 formed in the first end mirror 103 or reaches another relay mirror. Upon reaching the optical aperture 115, the light exits the optical multi-pass cell 100 through the apertures 107 and 115, where it is received by the optical detector 231. It should be appreciated that if relay mirrors are provided at more than one location, more than two beam patterns will be created before the light exits the sample cavity 109. Further, in other embodiments, the light may be reflected off from the same relay mirror more than one time to create more than two beam patterns. As is well known in the art, as the light propagates through the sample cavity 109 creating the first and at least second beam patterns, the path length is significantly increased. In addition, if a sample under test is provided in the sample cavity 109, a portion of the light's energy is absorbed by the sample. The energy absorbed by the sample can be determined using the optical detector 231 in order to analyze the sample under test, as is known in the art. An example reflection pattern is shown in FIG. 3.

Figure 3:
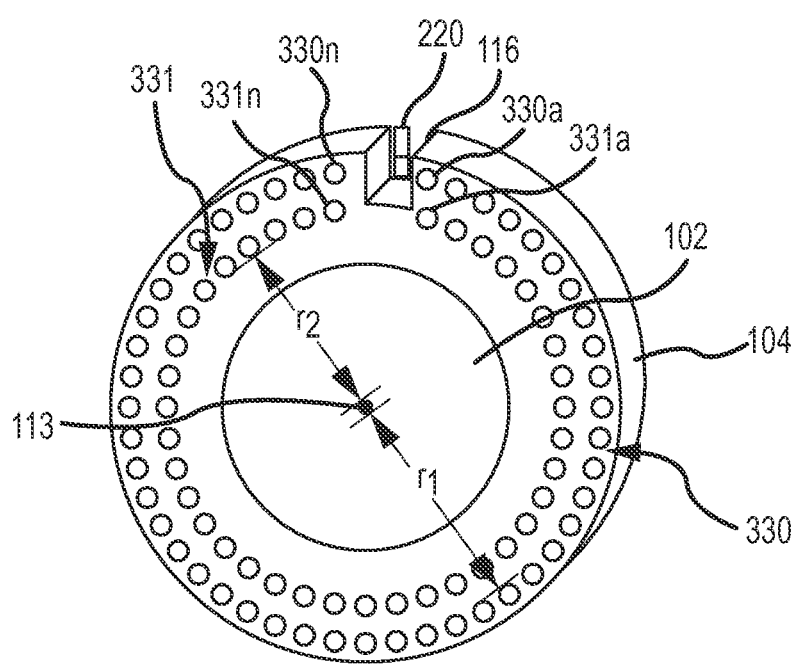
FIG. 3 shows a beam pattern on one of the end mirrors according to an embodiment of the invention.

FIG. 3 shows an example of a beam pattern obtained according to an embodiment of the invention. According to an embodiment of the invention, the outer beam pattern 330 is generated prior to the light being reflected off from the one or more relay mirrors 220. For example, the light may be introduced such that the light is introduced through the optical apertures 107 and 115 and directed towards position 330a where the light is first reflected. The light is reflected and refocused between the first and second end mirrors 103, 104 from a-n times with the last beam spot being reflected at position 330n. According to an embodiment of the invention, the light travels around the end mirrors 103, 104 from positions 330a-330n in a circular pattern at a distance $r_1$ from the optical axis 113. The pattern does not have to be circular however and any desired shaped pattern may be obtained by adjusting the radius of curvature of the first and second end mirrors 103, 104, the distance between the two end mirrors 103, 104, or the angle the light is introduced, for example. These adjustments used to configure the beam pattern are well known in the art and are taught for example by U.S. Pat. No. 5,291,265, which is hereby incorporated by reference. It should be appreciated that the analysis set forth in the '265 patent is merely one such example and other mathematical models are known for determining the specific beam pattern that will be generated by an optical multi-pass cell. The '265 patent is based in part on the work set forth by Herriott and coworkers as described in U.S. Pat. No. 3,253,226, which is also hereby incorporated by reference.

According to an embodiment of the invention, after the light reaches beam spot 330n, the light is reflected back towards the first end mirror 103. As the light is reflected back towards the second end mirror 104, the light enters the aperture 116, and is reflected off the one or more relay mirrors 220. As can be seen, the light enters the aperture 116 prior to reaching beam spot 330a a second time. Therefore, the light does not overlap, which could negatively affect the accuracy and add optical noise from the optical multi-pass cell as described above. The one or more relay mirrors 220 reflect the light at an angle different from the angle at which the light is reflected off from the first and second end mirrors 103, 104. As a result, a new beam pattern 331 is created. According to the embodiment shown, the new beam pattern 331 is closer to the optical axis of symmetry 113. For example, as shown, the first reflection pattern 330 is at an average distance $r_1$ from the optical axis of symmetry 113 while the second beam pattern 331 is at an average distance $r_2$ from the optical axis of symmetry 113, where $r_1 > r_2$. According to other embodiments, the one or more relay mirrors 220 may be configured to redirect the new beam pattern 331 such that the reflection pattern 331 is further from the optical axis of symmetry 113. Further, while both the first and second beam patterns 330, 331 are shown as circular, other shapes may be created. Further, the shapes of the first and second beam patterns 330, 331 may differ from one another. The new beam pattern 331 can travel around the first and second mirrors 103, 104 to create the second beam pattern 331 in a similar manner as the first beam pattern 330. According to the embodiment shown, once the light is reflected from position 331n back towards the first mirror 103, the light exits the sample cavity 109 through the apertures 115 and 107 where it is received by the optical detector 231. As can be seen in FIG. 3, the first and second beam patterns 330, 331 are at a distance from the optical axis 113 beyond the center rod 102. Therefore, while the center rod 102 can decrease the volume of the sample cavity 109, the center rod 102 does not interfere with the light.

As is generally known in the art, if a sample under test is introduced into the sample cavity 109 while the light is propagating through the sample cavity 109 as described above, a portion of the light's energy will be absorbed by the sample under test. According to an embodiment of the invention, the optical detector 231 and/or the external processing system can determine the amount of energy absorbed in order to analyze the sample under test as is known in the art.

Figure 4:
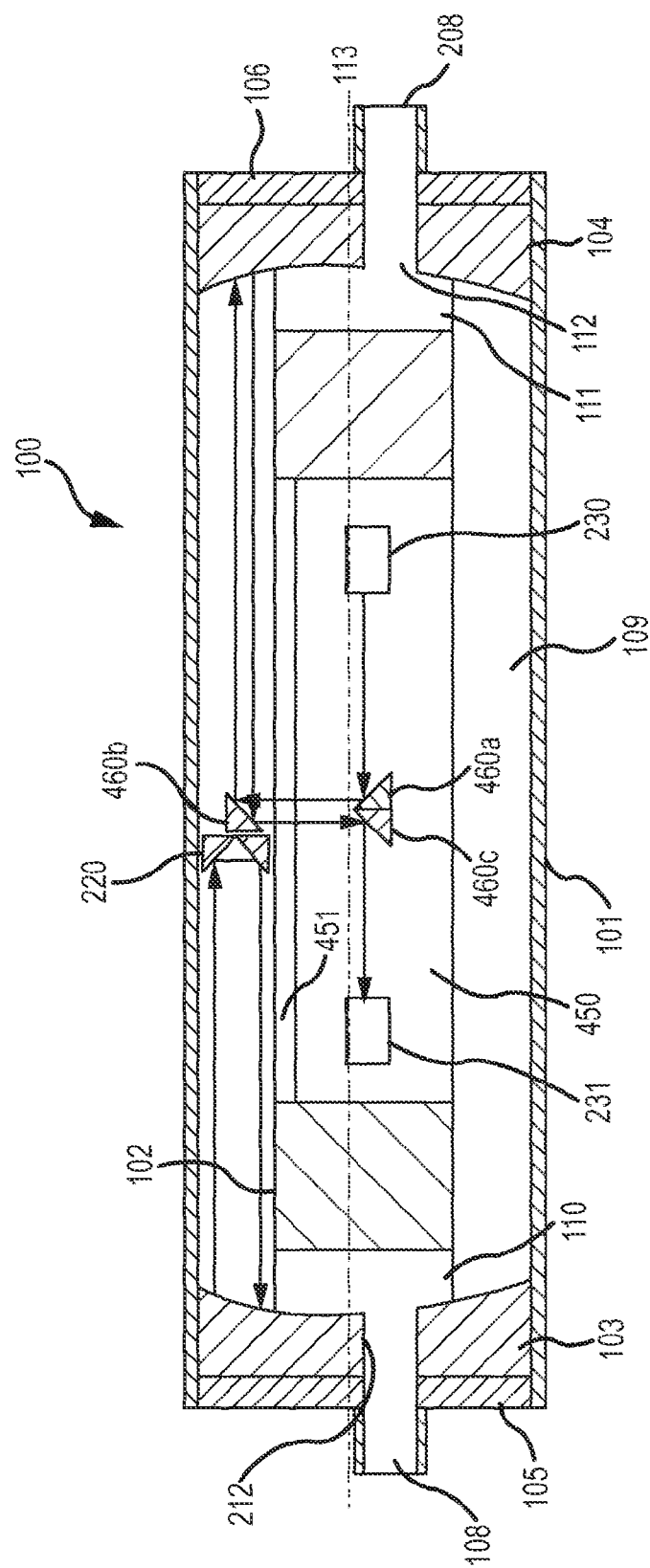
FIG. 4 shows a cross-sectional view of the optical multi-pass cell according to another embodiment of the invention.

FIG. 4 shows a cross sectional view of the optical multi-pass cell 100 according to another embodiment of the invention. In the embodiment shown in FIG. 4, the optical source 230 and optical detector 231 are located within the housing 101 rather than outside as in FIG. 1. More specifically, in the embodiment shown in FIG. 4, the optical source 230 and optical detector 231 are located within an internal cavity 450 formed in the center rod 102. According to an embodiment of the invention, the center rod 102 includes an at least partially optically transparent portion 451 that allows the light to exit and enter the internal cavity 450. While light can pass through the transparent portion 451, the sample medium under test cannot pass through the transparent portion 451. Rather the sample is limited to the sample cavity 109 formed by the housing 101 and the exterior surface of the center rod 102. As a result of the optical source 230 and optical detector 231 being positioned within the housing 101, the optical aperture 107 formed in the end cap and the aperture 115 formed in the first end mirror 103 can be omitted.

According an embodiment of the invention, in addition to the end mirrors 103, 104 and relay mirrors 220 described above, the multi-pass cell 100 can include one or more redirecting mirrors 460a-460c. The one or more redirecting mirrors 460a-460c can be positioned to redirect the light provided by the optical source 230 to the first and second end mirrors 103, 104 and back to the optical detector 231. According to an embodiment of the invention, the light is output by the optical source 230 and directed towards the first redirecting mirror 460a. The light is reflected off from the first redirecting mirror 460a towards the second redirecting mirror 460b. The light is then reflected off from the second redirecting mirror 460b towards one of the first or second end mirrors 103, 104. In the embodiment shown in FIG. 4, the light is directed from the second redirecting mirror 460b towards the second end mirror 104. According to an embodiment of the invention, the light is reflected between the first and second end mirrors 103, 104 as described above. The beam pattern travels around first and second end mirrors 103, 104 until the light reaches a relay mirror 220 of the one or more relay mirrors 220. According to the embodiment shown in FIG. 4, the relay mirror 220 is coupled to the housing 101 and positioned within the sample cavity 109. It should be appreciated that the relay mirror 220 could be positioned within the aperture 116 as in FIG. 1. Further, it should be appreciated that the relay mirror 220 could be positioned in the sample cavity 109 as shown in FIG. 4, in embodiments where the optical source 230 and optical detector 331 are located outside of the housing 101 as in FIG. 1. According to the embodiment shown in FIG. 4, the light reaches the one or more relay mirrors 220 after being reflected off from the first end mirror 103. However, it should be understood that the relay mirror 220 may be positioned such that the light reaches the relay mirror 220 after being reflected off from the second end mirror 104.

As described above, upon reaching the relay mirror 220, the light is reflected back towards the first reflective surface 103 at an angle that is different from the angle that the light is reflected off from the second reflective surface 103. As a result, a second beam pattern is provided in a similar manner as described above. The light is reflected between the first and second end mirrors 103, 104 at a distance away from the optical axis of symmetry 113 that is different from the distance of the first reflection pattern until the light reaches the second redirecting mirror 460b. Upon reaching the second redirecting mirror 460b from the second end mirror 104, the light is redirected towards the third redirecting mirror 406c. The light is then reflected off from the third redirecting mirror 406c towards the optical detector 231.

It should be appreciated that the optical source 230 and the optical detector 231 may be connected to suitable circuitry or other electronics as may be necessary or desired in order for the components to operate. The electronics may pass through the center rod 102, the housing 101, the end caps 105, 106, etc. However, the electronic connections have been omitted from the figures in order to simplify the drawings. It should be appreciated that the optical detector 231 may also be electronically coupled to one or more processors that can process the optical signal that is received by the optical detector 230.

The present invention provides an optical multi-pass cell 100 that can be formed in order to increase the optical path length to increase the signal-to-noise ratio over prior art systems. By positioning one or more relay mirrors so as to intercept the beam of light before the beam spots begins to overlap, at least a second beam pattern can be created that further increases the effective path length of the light within the sample cavity. Further, a center rod 102 may be positioned within the housing 101 in order to decrease the effective volume of the sample cavity 109. By decreasing the effective volume of the sample cavity 109, the actual sample volume can be reduced, and as a result, the time for replacing the sample volume and associated measurement time can be reduced. If a faster sampling time is not desired, however, a significantly smaller pump system may be employed that is capable to replace the sample volume in the same amount of time that it would take to replace the volume for a traditional multi-pass cell design of equivalent absorption path length.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other optical cells, and not just to the embodiments described above and shown in the accompanying figures. Accordingly, the scope of the invention should be determined from the following claims.

I claim:

1. An optical multi-pass cell (100), comprising:
a housing (101) defining a sample cavity (109) for receiving a sample under test;
first and second end mirrors (103, 104) positioned within the housing (101), separated by a distance, L, and facing one another coaxially to an optical axis (113) extending between the first and second end mirrors (103, 104), the first and second mirrors (103, 104) being configured to reflect a beam of light directed at one of the first or second end mirrors (103, 104) off-axis from the optical axis (113) one or more times between the first and second end minors (103, 104) through the sample cavity (109) at a first distance from the optical axis (113) to create a first beam pattern (330); and
one or more relay mirrors (220) positioned to intercept the beam of light and configured to reflect the beam of light such that at least a second beam pattern (331) is created between the first and second end mirrors (103, 104) at a distance from the optical axis (113) different from the first distance of the first beam pattern (330) such that the second beam pattern (331) does not overlap the first beam pattern (330).

2. The optical multi-pass cell (100) of claim 1, further comprising an aperture (116) formed in one of the first or second end mirrors (103, 104), wherein a relay mirror (220) of the one or more relay minors (220) is positioned within the aperture (116).

3. The optical multi-pass cell (100) of claim 1, further comprising first and second end caps (105, 106) coupled to the housing (101).

4. The optical multi-pass cell (100) of claim 3, further comprising an optical aperture (107) formed in the first end cap (105) and aligned with an aperture (115) formed in the first end mirror (103) for introducing the beam of light into the sample cavity (109) and/or extracting the beam of light out of the sample cavity (109).

5. The optical multi-pass cell (100) of claim 3, further comprising a first sample aperture (108) formed in the first end cap (105) and a second sample aperture (208) formed in the second end cap (106).

6. The optical multi-pass cell (100) of claim 1, further comprising a center rod (102) extending within the housing (101) and coupled to the first and second end mirrors (103, 104).

7. The optical multi-pass cell (100) of claim 6, further comprising one or more apertures (110) formed in the center rod (102) proximate the first end mirror (103).

8. The optical multi-pass cell (100) of claim 6, further comprising one or more apertures (111) formed in the center rod (102) proximate the second end mirror (104).

9. An optical multi-pass cell (100), comprising:
a housing (101) defining a sample cavity (109) for receiving a sample under test;
first and second end mirrors (103, 104) positioned within the housing (101), separated by a distance, L, and facing one another coaxially to an optical axis (113) extending between the first and second end mirrors (103, 104), the first and second mirrors (103, 104) being configured to reflect a beam of light directed at one of the first or second end mirrors (103, 104) off-axis from the optical axis (113) one or more times between the first and second end mirrors (103, 104) through the sample cavity (109) at a first distance from the optical axis (113) to create a first beam pattern (330);
one or more relay mirrors (220) positioned to intercept the beam of light and configured to reflect the beam of light such that at least a second beam pattern (331) is created between the first and second end mirrors (103, 104) at a distance from the optical axis (113) different from the first distance of the first beam pattern (330);
a center rod (102) extending within the housing (101) and coupled to the first and second end mirrors (103, 104);
an internal cavity (450) and an optically transparent portion (451) formed in the center rod (102);
an optical source (230) and an optical detector (231) located in the internal cavity (450);

one or more redirecting mirrors (460*a*, 460*c*) located in the internal cavity (450); and one or more redirecting mirrors (460*b*) located in the sample cavity (109), the redirecting mirrors (460*a*-460*c*) being configured to reflect a beam of light from the optical source (230) towards one of the first or second end mirrors (103, 104) and reflect the beam of light from one of the first or second end mirrors (103, 104) towards the optical detector (231).

10. A method for forming an optical multi-pass cell including a housing defining a sample cavity, comprising steps of:

positioning a first end mirror within the housing at a first end;

positioning a second end mirror within the housing at a second end, such that the first and second end mirrors are separated by a distance and face one another coaxial to an optical axis that extends between the first and second end mirrors and wherein the first and second end mirrors are configured to reflect a beam of light directed at one of the first or second end mirrors off-axis from the optical axis one or more times between the first and second end mirrors through the sample cavity at a first distance from the optical axis to create a first beam pattern; and positioning one or more relay mirrors to intercept the beam of light and reflect the beam of light such that at least a second beam pattern is created between the first and second end mirrors at a distance from the optical axis different from the first distance of the first beam pattern such that the second beam pattern does not overlap the first beam pattern.

11. The method of claim 10, further comprising steps of:

forming an aperture in one of the first or second end mirrors; and positioning a relay mirror of the one or more relay mirrors within the aperture.

12. The method of claim 10, further comprising a step of coupling first and second end caps to the housing.

13. The method of claim 12, further comprising steps of:

forming an optical aperture in the first end cap; and forming an aperture in the first end mirror to align with the optical aperture.

14. The method of claim 12, further comprising steps of:

forming a first sample aperture in the first end cap; and forming a second sample aperture in the second end cap.

15. The method of claim 10, further comprising a step of extending a center rod within the housing.

16. The method of claim 15, further comprising a step of forming one or more apertures in the center rod proximate the first end mirror.

17. The method of claim 15, further comprising a step of forming one or more apertures in the center rod proximate the second end mirror.

18. A method for forming an optical multi-pass cell including a housing defining a sample cavity, comprising steps of:

positioning a first end mirror within housing at a first end;

positioning a second end mirror within the housing at a second end, such that the first and second end mirrors are separated by a distance and face one another coaxial to an optical axis that extends between the first and second end mirrors and wherein the first and second end mirrors are configured to reflect a beam of light directed at one of the first or second end mirrors off-axis from the optical axis one or more times between the first and second end mirrors through the sample cavity at a first distance from the optical axis to create a first beam pattern;

positioning one or more relay mirrors to intercept the beam of light and reflect the beam of light such that at least second beam pattern is created between the first and second end mirrors at a distance from the optical axis different from the first distance of the first bean pattern;

extending a center rod within the housing;

forming an internal cavity and an optically transparent portion in the center rod;

positioning an optical source and an optical detector in the internal cavity;

positioning one or more redirecting mirrors in the internal cavity; and positioning one more redirecting mirrors in the sample cavity, wherein the redirecting mirrors are configured to reflect a beam of light from the optical source towards one of the first or second end minors and reflect the beam of light from one of the first or second end mirrors towards the optical detector.

\* \* \* \* \*